US00RE35348E

United States Patent [19]

Georgi

[11] E Patent Number: Re. 35,348

[45] Reissued Date of Patent: Oct. 8, 1996

[54] ARTIFICIAL SYSTEM AND METHOD FOR BREEDING HEMATOPHAGOUS INSECTS

[75] Inventor: Jay R. Georgi, Freeville, N.Y.

[73] Assignee: Cornell Research Foundation, Inc., Ithaca, N.Y.

[21] Appl. No.: 186,800

[22] Filed: Jan. 25, 1994

Related U.S. Patent Documents

Reissue of:

[64] Patent No.: 5,133,289
Issued: Jul. 28, 1992
Appl. No.: 755,141
Filed: Sep. 5, 1991

[51] Int. Cl.[6] ..... A01K 67/00

[52] U.S. Cl. ..... 119/6.6

[58] Field of Search ..... 119/15, 17, 6.6, 119/6.5, 174

[56] References Cited

U.S. PATENT DOCUMENTS

| | | | |
|---|---|---|---|
| 3,893,420 | 7/1975 | Andreev et al. | 119/1 |
| 4,850,305 | 7/1989 | Georgi et al. | 119/1 |

OTHER PUBLICATIONS

Hinkle, N. C., et al, Flea Rearing in Vivo and in Vitro for Basic and Applied Research, in Advances in Insect Rearing for Research and Pest Management, Anderson, T. E., et al (eds.), Westview Press, Boulder, 1992, pp. 119–130.

Rutledge, L. C. et al, Mosquito News, pp. 407–419, Dec. 1964.

Sgovina, K., Parasitenk, 7:539–571 (1935).

Totze, R., Zentralbl, Bakt Parasitenk Infekt. 132:382–384 (1934).

Wade, S. E., et al, J. Med. Ent., 25, No. 3, 186–190 (May 1988).

Bar-Zeev, M., et al., Entomol. Exp. & Appl. 5:60–68, 1962.

Bernardo, M. J., et al., J. Med. Ent. 23, No. 6, 666–679, Dec. 1986.

Cerwonka, R. H., et al., J. Parasitology, 44, No. 5, 565–566, 1958.

Galun, R., Life Sciences, 5:1335–1342, 1966.

Kartman, L., Experimental Parasitology, 525–537 (1954).

Lauer, D. M., et al., J. Med. Ent. 14, No. 5, 595–596 (Feb. 1978).

*Primary Examiner*—John G. Weiss

[57] ABSTRACT

A system for breeding fleas comprises a blood reservoir with a feeding membrane and a cage adjacent to the feeding membrane and containing a screen which supports the fleas during feeding, divides the cage into a feeding chamber and an egg collection chamber and provides access by the fleas between these chambers. The fleas are confined in the cage and stand on the screen to feed by penetrating the membrane with their mouth parts to obtain blood from the reservoir. The access between the feeding and egg collection chambers allows the cage to contain more fleas than if such access were not provided and open interiors of the feeding and egg collection chambers allow easy cleaning and egg collection.

12 Claims, 2 Drawing Sheets

ARTIFICIAL SYSTEM AND METHOD FOR BREEDING HEMATOPHAGOUS INSECTS

Matter enclosed in heavy brackets [ ] appears in the original patent but forms no part of this reissue specification; matter printed in italics indicates the additions made by reissue.

TECHNICAL FIELD

This invention is directed to the in vitro breeding of fleas, i.e. the breeding of fleas in artificial systems where they do not feed on animal hosts. The fleas produced by the system and method herein are useful for research purposes, e.g. to test the effect of growth regulators or toxicants, to study the transmission of blood borne disease organisms and parasites to fleas, to determine causes of allergies in animals bitten by fleas, to develop antiflea vaccines, and to isolate and maintain strains of fleas possessing distinctive biological traits such as drug resistance or allergenicity. The invention reduces the need for animal hosts thereby decreasing the cost of research and public relations problems associated with using animals in research. The invention also allows more exact control of conditions compared to breeding programs relying on feeding on live hosts.

BACKGROUND OF THE INVENTION

In vitro feeding of hematophagous insects, including fleas, using systems comprising a cage, a food supply in a container with a feeding membrane and a food supply temperature control system have long been known. Such a system may comprise a Rutledge-type membrane feed (described in Rutledge, L. C., et al Mosquito News, pp. 407–419, Dec., 1964) with host blood therein as food with water circulating therethrough to control the food (blood) temperature. Successful feeding of fleas has been reported by Bar-Zeev M. et al, Entomol. Exp. & Appl. 5:60–68, 1962; Cerwonka R. H. et al, J. Parasitol. 44:565–566, 1958; Galun, R., Life Sci. 5:1335–1342, 1966; Kartman, L., Expr. Parasitol. 3:525–537, 1954; Lauer, D. M. et al, J. Med. Entomol. 14:595–596, 1978; and Totze, R., Zentrabl. Bakt. parasitenk. Infekt. 132:382–384, 1934. Only Lauer et al mention observing mating, ovipositing and viable larval production, but they do not report reproduction outputs. Lauer et al report feeding times of 1–5 hours in a feeding chamber which is a 2 cm diameter by 5 cm high back plastic cylinder installed directly above a feeding membrane.

One object of this invention is to provide a system and method for practical breeding of fleas, utilizing an artificial system and method, i.e., a system and method which does not rely on feeding on a host animal. The term "practical breeding" of fleas is used herein to mean breeding to obtain a reproduction output at least 10% of the reproduction output of fleas feeding on host animals. While breeding of mosquitoes and flies has been obtained based on artificial systems, the breeding of fleas relying on such systems is much more difficult.

While the Lauer et al article described above reports breeding of fleas relying on an artificial system, the conditions utilized do not provide practical breeding.

Georgi et al, U.S. Pat. No. 4,850,305, describes apparatus and method for practical breeding of fleas, relying either on a flea cage with a height dimension to restrict jumping by fleas housed therein or on a flea cage containing fibrous material such as animal hair to provide pathways permitting the fleas to walk thereon to the feeding location. The system with the flea cage of restricted height dimension is substantially limited in the number of fleas that can be accommodated. The system with the flea cage containing animal hair provides cage cleaning and egg collection difficulties.

It is a further object of this invention to provide a system and method for the practical breeding of fleas which allows for facile cleaning and egg collecting and which in a preferred embodiment provides flexibility in the number of fleas that can be housed in a given dimension cage.

SUMMARY OF THE INVENTION

It has been discovered herein that the above objects are obtained by utilizing some of the characteristics of the systems and methods of the Georgi et al patent, but instead providing a flea cage with a substantially planar scaffold means in its interior.

The system herein for breeding fleas without providing access of the fleas to host animals comprises (a) containing means for functioning in combination with means penetrable by flea mouth parts for feeding, to provide a blood reservoir means, (b) cage means for housing fleas for breeding, having an interior (i), a top end (ii) for juxtaposition to said penetrable means and allowing access by flea mouth parts to said penetrable means for feeding, and a bottom end (iii), (c) substantially planar scaffold means suspended in said interior (b)(i) to support fleas for feeding.

In a preferred embodiment of the system herein, the scaffold means is a one-pie reticulated member which divides the interior of the cage into a feeding chamber (b)(iv) and an egg-collecting chamber (b)(v) and has interstices allowing fleas access between chambers (b)(iv) and Co)(v):

In a more preferred embodiment of the system herein, said cage means (b) includes a sidewall having an inner surface containing a peripheral shoulder which removably receives said scaffold means (c), the location of said shoulder below said top end (b)(ii) and the thickness of the scaffold means (c), defining a height dimension for the chamber (b)(iv).

In a still more preferred embodiment of the system herein, the cage means (b) is circular in cross-section and comprises (d) a first annular sidewall piece having an inner wall (d)(i) and an outer wall (d)(ii) having an upper larger diameter portion (d)(iii) and a lower smaller diameter portion (d)(iv)joined by a shoulder portion (d)(v), and having an open top end (d)(v) and a reticulated bottom end (d)(vii), and (e) a second annular sidewall piece having a topwall (e)(i) for mating with shoulder portion (d)(v) and an inner wall (e)(ii) with an upper larger diameter portion (e)(iii) dimensioned to abut portion (d)(iv) and a lower smaller diameter portion (e)(iv) defining an inner diameter of the cage means Co) joined by a shoulder portion (e)(v), and having an open top end (e)(vi) and a reticulated bottom end (e)(vii);

the portion (d)(iv) having a height dimension and the portion (e)(iii) having a height dimension, such that the height dimension of (e)(ii) is more than that of the portion (d)(iv) by an amount which, minus the thickness of (d)(vii) and the thickness of (c), defines the height dimension of the chamber (b)(iv), the scaffold means (c) being removably positioned on portion (e)(v) and the portion (d)(v) being removably positioned on topwall (e)(i), to form the cage means (b) with the scaffold means (c) positioned therein.

The method herein for breeding fleas without having the fleas feed on a host animal, comprises the steps of (a) confining the fleas in a breeding zone having a feeding end and an egg collection end, (b) providing an inanimate flea-accessible source of host animal blood at a selected temperature at said feeding end;

(c) providing in the breeding zone a scaffold means to support fleas, for feeding at said feeding end;

(d) dividing the breeding zone with the scaffold means into an upper feeding zone having an open interior and including said feeding end, and a lower egg collection zone having an open interior and including said egg collection end, (e) providing access by fleas between the feeding zone and the egg collection zone;

thereby to foster feeding, mating and egg production.

Utilizing a substantially planar scaffold means instead of animal hair allows easy cleaning of the cage and easy egg collection.

Utilizing a scaffold means which divides the flea cage into a feeding chamber and an egg collecting chamber and provides access between the chambers allows more fleas to be present than in the case of the restricted height flea cage of the Georgi et al patent.

The term "substantially planar" is used to mean that the scaffold means, which preferably is reticulated, has a surface which is substantially parallel to the feeding membrane, as distinguished from individual fibers as used in a device in the Georgi et al patent.

BRIEF DESCRIPTION OF THE DRAWINGS

While the specification concludes with claims particularly pointing out and distinctly claiming the subject matter of the present invention, it is believed the invention will be better understood from the following description taken in connection with the accompanying drawings, in which:

DETAILED DESCRIPTION

Figure 1:
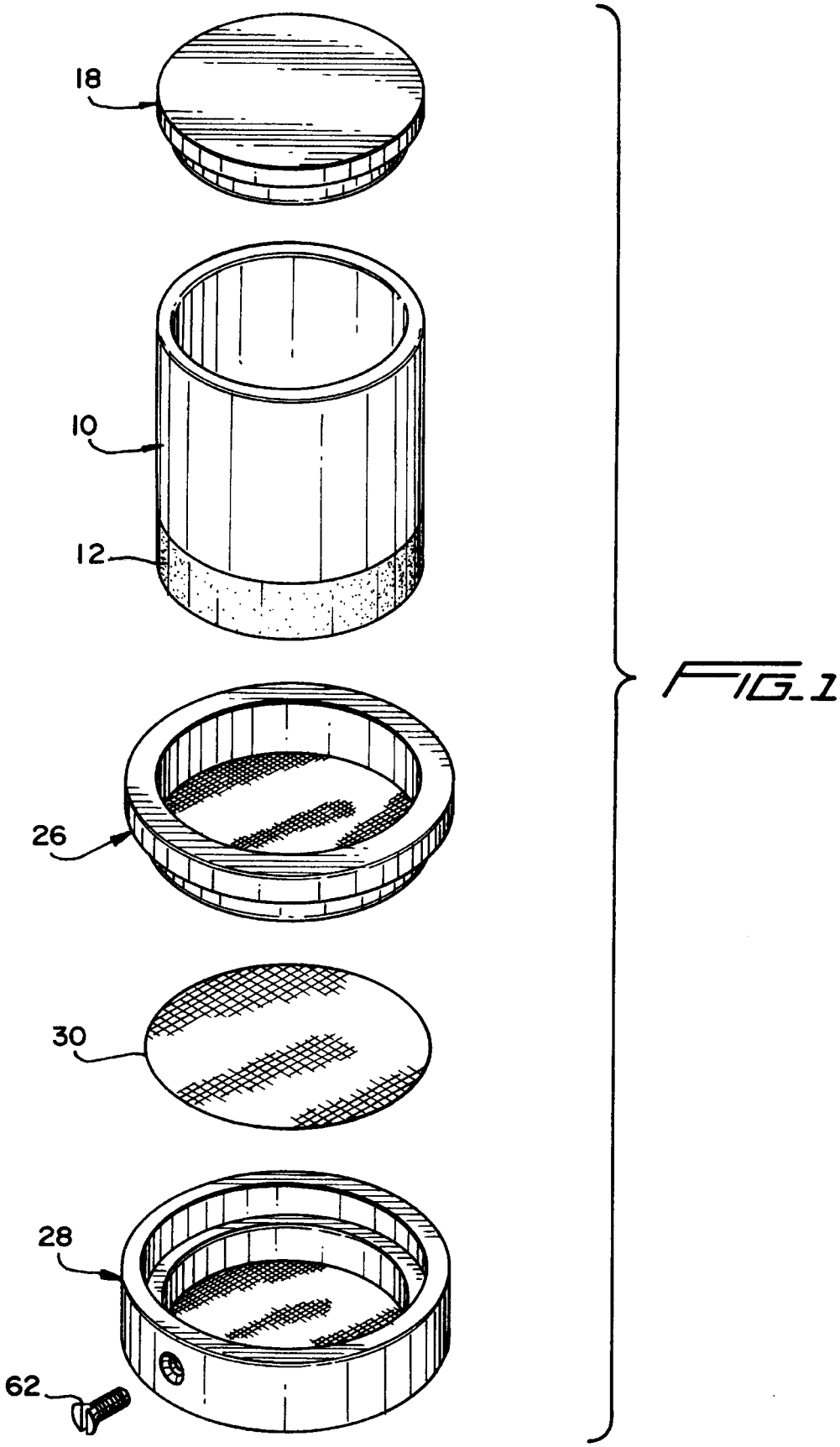
FIG. 1 is an exploded perspective view of pans assembled to provide a preferred system within the scope of the invention, with means for maintaining the temperature of the blood omitted.
Figure 2:
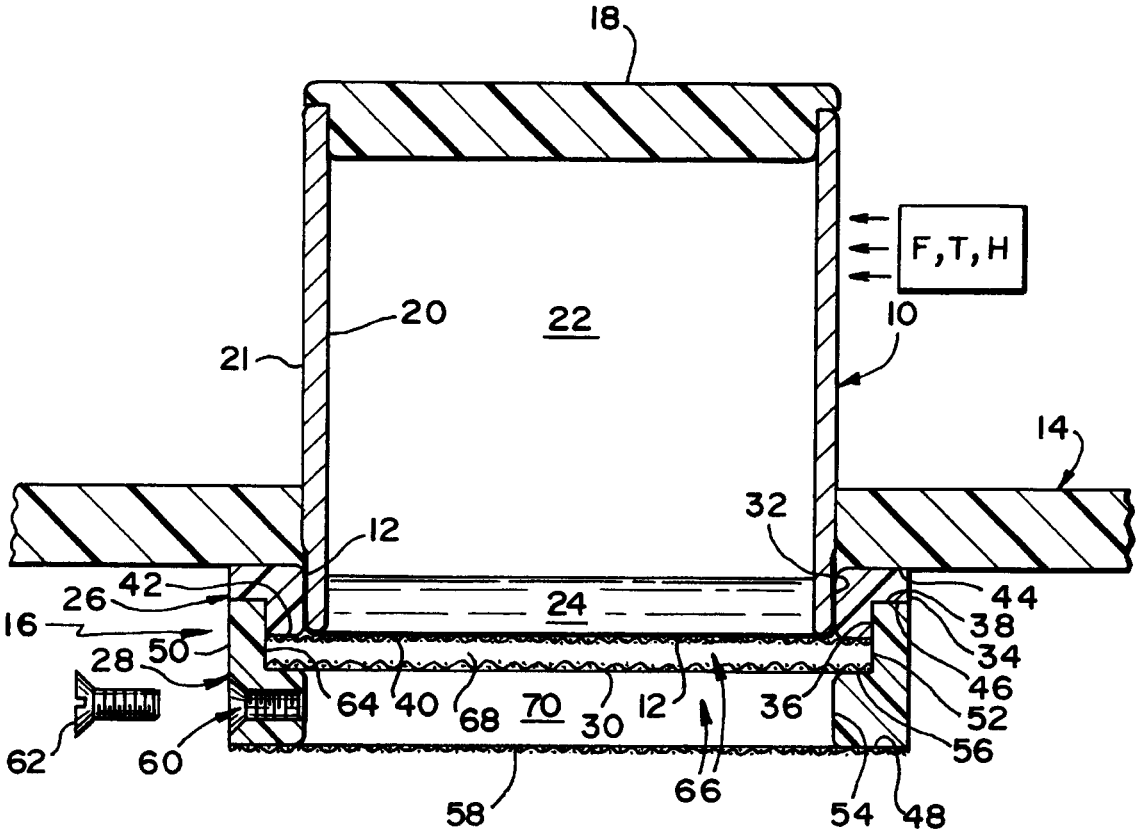
FIG. 2 is a vertical sectional view of the apparatus of FIG. 1 containing blood and with the means for maintaining the temperature of the blood schematically depicted.

Turning now to the embodiment depicted in FIGS. 1 and 2, said embodiment comprises a blood containing means 10 associated with a membrane 12 and a blood warming device 14 and an assembly 16 constituting a flea cage.

The means 10 is an open-ended cylindrical sleeve and has a lid 18. The means 10 is sometimes referred to hereinafter as sleeve 10.

Stretched over the bottom of the sleeve 10 is the membrane 12 which is preferably maintained in place by friction.

An inner sidewall 20 of sleeve 10 and the portion of membrane 12 adjacent the bottom of sleeve 10 form a blood chamber or reservoir 22. Blood is readily introduced into the blood chamber or reservoir 22 after assembly of the apparatus by removing lid 18 and feeding blood through the top opening of sleeve 10 to form a body of blood 24 therein. The portion of the membrane 12 adjacent the bottom of sleeve 10 constitutes the feeding end of reservoir 22 and functions to support the body of blood 24 in reservoir 22. Which serves as the food source for fleas confined in the flea cage 16 for mating and egg production purposes. The membrane 12 is readily penetrable by flea mouth parts for feeding and is self-sealing after feeding and is preferably composed of Parafilm which adheres to outer sidewall 21 of sleeve 10 without external support.

The reservoir 22 is in heat exchange relation with the warming device 14 which is schematically depicted. Preferably this warming device is a box having holes cut out of the bottom to accommodate the sleeves 10 of a plurality of devices, with a silent running 26 to 50 cubic foot per minute, 3 to 4 inch fan *F* a cartridge heater, *H* and a thermostat *T* to control the heater, *H* placed inside the box *as schematically depicted in FIG. 2.*

Turning now to the flea cage 16, the parts constituting it are best depicted in the exploded view of FIG. 1 and the assembled flea cage is depicted in FIG. 2. As depicted in FIGS. 1 and 2, the flea cage 16 is readily constructed utilizing two annular sidewall members 26 and 28, and the scaffold means is provided by a substantially planar one-piece reticulated member The member 26 includes a top end 44, a bottom end 42, an inner wall 32, and an outer wall with an upper larger diameter portion 34 and a lower smaller diameter portion 36 joined by a downwardly facing shoulder 38, and is open at its top end 44 and is covered at its bottom end 42 with reticulated member 40 which preferably is constructed of monofilament nylon screencloth.

The member 28 includes a top end 46, a bottom end 48, an outer wall 50, and an inner wall having an upper larger diameter portion 52 and a lower smaller diameter portion 54 joined by an upwardly facing shoulder $6 and is open at its top end 46 and is covered at its bottom end 48 with reticulated member 58 which preferably is constructed of monofilament nylon screencloth. The member 28 contains a fill hole 60 which is closed by a screw 62.

The reticulated member 30 is a screen preferably made of monofilament nylon screencloth.

The diameter of wall 52 is selected to afford clearance for membrane 12 wrapped around sleeve 10. In preferred embodiment the membrane adheres very securely to sleeve 10 and requires no external support.

The diameter of wall 36 is selected to abut the portion 52 in such a manner as to produce a sliding fit with sufficient resistance to require torque applied by both hands for undoing.

The diameters of portions 52 and 54 define the inner diameters of flea cage 16.

The members 26 and 28, except for the reticulated portions, are preferably constructed of transparent acrylic plastic and in a preferred embodiment the peripheries of the nylon screencloth reticulated members are readily joined to the acrylic ting by cementing.

The cage 16 is assembled by suspending member 30 about its periphery on shoulder 56 and then inserting the lower end of member 26 into the upper end of member 28 and supporting shoulder 38 on the top end 46 of member 28. This construction eliminates clefts to which fleas have access. This is an advantage over the assembled embodiment of the Type C cage depicted in Wade, S. E., et al, Journal of Medical Entomology, Vol. 25, No. 3, pp. 186–190. This Type "C" cage has such clefts and fleas entered these and became trapped.

The cage 16 is assembled with the other parts as follows: The membrane 12 is positioned over the bottom of sleeve 10 and wrapped around it. Then this assembly is inserted into the upper end of member 26 so that the portion of member 12 which overlies the lower opening in sleeve 10 is juxtaposed to the reticulated member 40. Then blood, preferably prewarmed, is filled into the sleeve 10 so as to accumulate into a body 24 at the lower end of sleeve 10 on top of the portion of membrane 12 which overlies the lower opening in sleeve 10. Then the lid 18 is applied and the [sleeve 12] *sleeve 10* is inserted into the warming device 14. To maintain the blood in body 24 at operating temperature, the cartridge heater in device 14 is turned on and the fan in device 14 is turned on, and the thermostat in device 14 is set at the preselected temperature.

The member 40, a lower portion 64 of portion 52, the portion 54 and the member 58 define a breeding chamber 66 which is divided by the member 30 into a feeding chamber 68 and an egg collection chamber 70.

On assembly of the system, the membrane 12 bounding the body of blood 24 constitutes the feeding end of the blood reservoir and reticulated means in the form of member 40 constitutes the feeding end of chamber 68.

The height dimension of the portion 52 is greater than the height dimension of the portion 36 by an amount which defines the height dimension of the feeding chamber 68 once the thicknesses of the member 40 and the member 30 are taken into account.

The member 30 functions as a scaffold which supports fleas for feeding, allowing them secure footing while penetrating membrane 12 with their mouth parts to feed on blood from body of blood 24. In other words, fleas supported on the scaffold means do not have to leap to reach the membrane 12. Without the scaffold, a feeding flea is easily dislodged by collision with nonfeeding mobile fleas.

The interstices in member 40 are sized to allow insertion of flea mouth parts therethrough to penetrate through membrane 12 into the body of blood 24 for feeding, but to prevent escape of the fleas therethrough.

The interstices in member 30 are sufficiently large to allow the fleas to pass back and forth between chambers 68 and 70 but are preferably small enough to maximize the amount of structure available to support fleas for feeding.

The interstices in member 58 are sized to prevent escape of fleas and flea eggs from chamber 70 but to allow passage of ambient air into chambers 70 and 68 to provide adequate ventilation to prevent condensation of vapor.

The height dimension of chamber 68 is sized to allow fleas to be supported while feeding. In other words, the dimension is such that leaping by fleas standing on the member 30 is not required for them to feed but not so small that the member 30 loses its function of preventing dislodgement of feeding fleas by collision with nonfeeding mobile fleas.

The height dimension on the chamber 70 is uncritical, but it should be sufficiently large to allow room for fleas to move to and from the feeding chamber 68 and for accumulation of their eggs and fleas over a period of 48 hours.

The diameter of the sleeve 10 is uncritical. A diameter of 2 inches has been found to fit the hand for the purpose of applying the membrane.

Where the fleas being bred are Ctenocephalides felis or fleas of similar size, the following dimensions are considered appropriate. The interstices in member 40 range from 250 to 400 microns and are preferably 300 microns. The interstices in member 30 range from about 0.7 to about 1.1 mm and are preferably 1.0 mm. The interstices in member 58 range from 15 to 30 microns and are preferably 30 microns. The height dimension of chamber 68 ranges from 0.9 to 1.1 mm and preferably is 1.0 mm. The height dimension of chamber 70 conveniently ranges from ½ inch to 1 inch and very conveniently is one-half inch. The inner diameter of sleeve 10 adjacent its base can range, for example, from about 1½ to 3 inches. The height of sleeve 10 conveniently ranges from about 1½ to 2½ inches and very appropriately is about 2 inches. A suitable warming box can be, for example, 16 inches×16 inches×9 inches (high) and is made of acrylic sheet, nominally ⅜ inch thick.

Preferred practice utilizing the apparatus of FIGS. 1 and 2 is as follows:

A first method of use comprises the following. The device is disassembled. The fleas are immobilized to dormant state for transfer into the apparatus for carrying out a process herein, by refrigerating them, e.g. by exposure to 4° C. for 30 minutes or by contacting them with $CO_2$ gas. The immobilized fleas are placed on member 58. Then member 30 is suspended about its periphery on shoulder 56 of member 28 and the lower end of member 26 is inserted into the upper end of member 28. Then appropriate film for the membrane 12 is positioned over the bottom end of sleeve 10 and wrapped around the bottom outside portion of sleeve 10, and excess film, that is, beyond that which would extend above wall 44, is trimmed and the assembly is inserted into member 26. Then blood is added into sleeve 10 and lid 18 is applied. Then the assembly is positioned so that the sleeve 10 extends into warmer 14 as depicted in FIG. 2, and the warmer 14 is activated (i.e. the cartridge heater and fan are turned on and the operation of the cartridge heater is controlled by the thermostat).

A second method of use is the same as the above-described first method except that the fleas are not immobilized (as by cold or $CO_2$ contact) and are introduced onto member 58 by dumping fully conscious from a hopper while suction is applied to member 58, e.g. using a household vacuum cleaner (e.g. a 1.6 HP Kenmore). Then screen 30 is positioned on member 28, etc.

In a third method of use the apparatus is assembled before the fleas are inserted. The fleas are introduced via a suction tube (whereby counting of the number of fleas as they are picked up is possible) into fill hole 60, and the fleas are drawn into the flea cage 16 from said tube by the application of suction to screen 58 as described above. Finally, fill hole 60 is occluded by screw 62.

The membrane 12 is readily changed by removing the assembly from the warmer 14, inverting the assembly to dump the body of blood, then removing sleeve 10 together with its associated membrane 12, discarding the membrane 12, applying a new membrane 12 to sleeve 10, inserting the sleeve and associated film into member 26, trimming the excess film, adding blood into sleeve 10 atop the new membrane 12, and inserting the assembly into warmer 14.

Cleaning and egg collection are readily carried out by removing the cage and disassembling it, and collecting the eggs and feces into a petri dish. During this procedure the fleas jump out of the apparatus and are readily collected and installed in a clean cage.

Other information about the apparatus includes the following:

The sleeve 10 is preferably of aluminum or other heat conductive metal. The lid 18 is constructed of acrylic plastic but is also readily constructed of other materials including those that are good conductors of heat.

Other types of warmers may appropriately be used besides the one specifically described above. For example, a heat exchanger relying on a liquid heat exchange agent can be used. If desired, a Rutledge insect blood feeder as described in Georgi et al U.S. Pat. No. 4,850,305 can be used in place of sleeve 10 and warmer 14. Other blood feeden may also be used which contain a blood reservoir wall structure adapted to join with means penetrable by flea mouth parts for feeding.

The diameter of sleeve 10 is preferably such that the sleeve is not awkward to handle.

The membrane 12 should have a thickness at the location of feeding which is penetrable by the fleas for feeding on blood thereabove, normally from 0.001 to 0.005 inches. Parafilm, as indicated above, is a preferred material of construction for the membrane; this is because it readily adheres to sleeve 10 without external support and has been found to be useful for feeding without leakage occurring over a suitable feeding period. Parafilm is described in the Concise Chemical and Technical Dictionary (1974 edition) edited by H. Bennett as paraffin wax modified with an elastomer to give a flexible, thermoplastic sheet or film and by a representative of the manufacturer as composed of a blend of wax, elastomer and polyolefin. Other membranes besides Parafilm membranes indicated in literature to be useful for blood feeders are natural membranes including membranes made of mouse, rat, rabbit, flying squirrel or chicken skin, cattle cecum ("Silverlight" or Baudruche), sausage casing, condom material (sheep casing), and artificial membranes of Cellophane, Saran Wrap, agar, gold beater, and gutta percha. In a preferred execution of the invention where Parafilm of initial thickness of 0.005 inches is used for the membrane, it is drawn to a thickness of 1.5 mils on application to sleeve 10.

The material of construction for each of members 40, 30 and 58 is preferably screencloth that is commercially available and can be of metal or plastic, and preferably is of nylon (Nitex Screening Fabric). Aluminum mesh is also suitable. The material and construction should provide the necessary structural strength.

The wall structure of the flea cages is preferably of transparent material to allow viewing but can be of opaque material. Acrylic plastic is a preferred material of construction. Other suitable materials of construction include, for example, polyvinyl chloride, polyethylene, polypropylene and Teflon.

In the above-described embodiments the flea cages are made from parts machined to fit together with friction joints. However, other assembly/disassembly means can be provided, such as threads or pins.

Other information about the process herein is as follows:

The process herein is considered to be applicable to all species of fleas. It is especially useful in regard to fleas of economic importance to dogs, oats and humans, namely, Ctenocephalides felis, Ctenocephalides canis, Xenopsylla cheopis and Pulex irritans.

The hosts reported for Ctenocephalides felis include dog, cat, man, cattle, buffalo, sheep, goat, racoon, gray fox, red fox, coyote, bobcat, jackal, opossum, shorttailed shrew, rabbit, rat, red squirrel, hedgehog, greater yellow bat, mongoose, and common myna.

The hosts reported for Ctenocephalides canis include dog, cat, man, gray fox, coyote, ground squirrel, rat, striped skunk, buffalo, sheep, goat and opossum.

The hosts reported for Xenopsylla cheopis include rodents, such as the rat and mouse, man, sheep, goat, shrew, and mongoose.

The hosts reported for Pulex irritans include man, pig, prairie dog, rat, badger, rabbit, sheep, goat, cattle, deer, dog, cat, skunk, coyote, gray fox, bobcat, desert kit fox, weasel, opposum, chicken, burrowing owl and cuckoo.

The blood for use as feed should be the blood of a host animal. For C. felis, the preferred blood is dog blood or cattle blood which have been found to be equally effective. While cat blood is useful for C. felis, it. is difficult to obtain in sufficient quantity even for moderate usage and is expensive.

The blood is preferably used in conjunction with an anticoagulant such as 20% sodium titrate used, for example, in an amount of 35 ml of 20% sodium citrate per liter. The blood is readily stored under refrigeration, e.g. at 4° C., for up to two weeks prior to use and is storable for even a longer period if drawn under sterile conditions.

The temperature of the blood in the process herein preferably is maintained in the range of 35° C. to 40° C. Appropriate temperature is readily provided by setting the thermostat in warmer 14 at 38°–40° C.;

Twenty-four hours appears to be the practical limit for replacement of the blood in the process herein because if the blood is left longer, it clots and bacterial contamination increases.

The male to female ratio of the fleas inserted into the flea cages for the process herein preferably ranges from 1:10 to 1:1.

Preferably, the fleas should be provided continuous access to the host animal blood food source for at least 18 hours and a very preferred continuous access period ranges from 22 to 24 hours. About twenty-four hours of continuous-access is the practical limit since, as indicated above, the practical limit for replacement of the blood appears to be 24 hours.

The life span of the fleas determines the maximum time over which breeding is carried out. For most fleas, this period is about a month.

Production of fleas from eggs is readily carried out by conventional methods. In a preferred method, collected eggs are placed on autoclaved sand in a 100×25 mm plastic petri dish in an incubator at 27° C. and 80–85% relative humidity. After two days, the eggs hatch into larvae and are maintained in the incubator and supplied with ground dried cattle blood for food (the dried blood is added every other day). After 13–16 day, the cultures are sieved to recover pupae. The pupae are placed in tissue culture flasks with the caps modified to include nylon mesh with 300 micron interstices for admission of moist incubator air. The pupae in said modified flasks are maintained in the incubator at 27° C. and 80–85% relative humidity whereupon the pupae develop into adult fleas. With the above procedure the eggs are converted into adult fleas within 14 days.

The following specific example is illustrative of the invention:

EXAMPLE

Eggs obtained from C felis on cats and dogs in Freeville, N.Y. were used to start laboratory colonies.

Eggs so obtained or produced by further generations were matured into adult fleas by the preferred procedure described above.

Adult fleas emerging from the pupal stage were transferred into cages as described in conjunction with FIGS. 1 and 2. The cages were used in conjunction with associated apparatus as depicted in FIGS. 1 and 2. For said assembly, the sleeve 10 is constructed of aluminum and is 2 inches in diameter and 2 inches in height, the interstices of member 40 are 300 microns, the interstices of member 30 are 1 mm, the interstices of member 58 are 30 microns, the thickness of member 40 is 0.008 inch, the thickness of member 30 is 0.025 inch (0.635 mm), the thickness of member 58 is 0.0025 inch, the height of chamber 68 is 0.039 inch (1.0 mm), and the height of chamber 70 is about one-half inch. The membrane 12 is formed of Parafilm of initial thickness of 0.005 inches and on application it is drawn to a thickness of 1.5 mils. The warmer 14 used comprises a box of dimensions 16 inches by 16 inches by 9 inches. The thermostat of the warmer is set at 38°–40° C. Each assembly was filled with 10 ml of blood daily and the membranes were changed daily. The blood was cattle blood collected in a liter bottle to which 35 ml of 20% sodium citrate was added. The blood was collected weekly and stored in a refrigerator at 4° C. for use within a week. The cages were cleaned and the eggs were collected every other day and matured into adult fleas by the preferred procedure described above. On cleaning and egg collection, reassembly and introduction of fleas was carried out. Two hundred to three hundred fleas were introduced into an assembly. From these 2000 to 3000 eggs were harvested at the two-day egg collection and cleaning time. This represents a reproduction output of about 33% of that of C felis fed on cats even neglecting attrition of fleas due to self-grooming of the cat hosts. The apparatus and method function to practically breed fleas.

Other variations will be evident to those skilled in the 4 art. Therefore, the scope of the invention is intended to be defined by the claims.

What is claimed is:

1. System for breeding fleas without having them feed on host animals, said system comprising (a) containing means for functioning in combination with means penetrable by flea mouth parts for feeding, to provide a blood reservoir means, (b) cage means for housing fleas for breeding, having an interior, a top end for juxtaposition to said penetrable means and allowing access by flea mouth parts to said penetrable means for feeding, and a bottom end, (c) substantially planar scaffold means removably suspended in said interior to support fleas for feeding and dividing said interior into a feeding chamber and an egg collecting chamber and having access means therein allowing fleas to pass back and forth between said chambers.

2. System as recited in claim 1, wherein said scaffold means (c) comprises a one-piece reticulated member.

3. System as recited in claim 2, wherein said cage means (b) includes a sidewall having an inner surface containing a peripheral shoulder which removably receives said scaffold means (c), the location of said shoulder below said top end and the thickness of said reticulated member (c) defining a height dimension for the feeding chamber.

4. System as recited in claim 3, wherein said cage means (b) is circular in cross-section and comprises (d) a first annular sidewall piece having an inner wall and an outer wall having an upper larger diameter portion and a lower smaller diameter portion joined by a shoulder portion, and having an open top end and a reticulated bottom end, and (e) a second annular sidewall piece having a topwall for mating with said shoulder portion of said first annular sidewall piece and an inner wall with an upper larger diameter portion dimensioned to abut said lower smaller diameter portion of said first annular sidewall piece and a lower smaller diameter portion defining an inner diameter for the cage means (b), joined by a shoulder portion, and having an open top end and a reticulated bottom end;

the lower smaller diameter portion of said first annular sidewall piece having a height dimension and the upper larger diameter portion of said second annular sidewall piece having a height dimension such that the height dimension of the upper larger diameter portion of said second annular sidewall piece is more than that of the lower smaller diameter portion of said first annular sidewall piece by an amount which, minus the thickness of the reticulated bottom end of said first annular sidewall piece and the thickness of said scaffold means defines the height dimension of the feeding chamber, the scaffold means (c) being removably positioned on the shoulder portion of said second annular sidewall piece and the shoulder portion of said first annular sidewall piece being removably positioned on the topwall of said second annular sidewall piece to form the cage means (b) with the scaffold means (c) positioned therein.

5. System as recited in claim 2, wherein said reticulated member has interstices ranging from about 0.7 mm to about 1.1 min.

6. System as recited in claim 2, wherein the feeding chamber has a height dimension ranging from 0.9 to 1.1 mm.

7. System as recited in claim 6, wherein said height dimension is 1.0 mm.

8. System as recited in claim 6, wherein the egg collection chamber has a height dimension ranging from ½ inch to 1 inch.

9. System as recited in claim 6, wherein said reticulated member has interstices ranging from about 0.7 mm to about 1.1 min.

10. Method for breeding fleas without having the fleas feed on a host animal, said method comprising the steps of (a) confining the fleas in a breeding zone having a feeding end and an egg collection end, (b) providing an inanimate flea-accessible source of host animal blood at a selected temperature at said feeding end, (c) providing in the breeding zone a scaffold means to support fleas for feeding at said feeding end;

(d) dividing the breeding zone with the scaffold means into an upper feeding zone having an open interior and including said feeding end, and a lower egg collection zone having an open interior and including said egg collection end; and (e) providing access by fleas between the feeding zone and the egg collection zone so that the fleas can pass back and forth between the feeding zone and the egg collection zone thereby to foster feeding, mating and egg production.

*11. An artificial blood feeder breeding system comprising*

*(a) heat conducting wall in conjunction with replaceable self-sealing membrane which is pentrable for feeding, to define at least one blood reservoir,*

*(b) at least one cage having an interior, a top end for juxtaposition to the self-sealing membrane to allow access to the self-sealing membrane, and a bottom end,*

*(c) a blood warming box containing at least one hole receiving said at least one blood reservoir heat conducting wall*

*(d) a fan,*

*(e) a heater, end*

*(f) a thermostat,*

*the fan (d), the heater (e) and the thermostat (f) being positioned in the blood warming box (c) and the operation of the heater (e) being controlled by the thermostat (f).*

*12. The artificial blood feeder breeding system of claim 11 wherein each cage is associated with a sleeve constituting said heat conducting wall.*

* * * * *

UNITED STATES PATENT AND TRADEMARK OFFICE

CERTIFICATE OF CORRECTION

PATENT NO. : Re. 35,348
DATED : October 8, 1996
INVENTOR(S) : Jay R. Georgi

It is certified that error appears in the above-indentified patent and that said Letters Patent is hereby corrected as shown below:

Claim 8 (column 10, line 38), change "1/2" to --1/4--.

Claim 11 (column 10, line 66), change "pentrable" to --penetrable--.

Signed and Sealed this

Eighteenth Day of February, 1997

*Attest:*

Bruce Lehman

BRUCE LEHMAN

*Attesting Officer*

*Commissioner of Patents and Trademarks*